United States Patent
Samson et al.

(10) Patent No.: US 9,075,252 B2
(45) Date of Patent: Jul. 7, 2015

(54) REMOTE WORK METHODS AND SYSTEMS USING NONLINEAR LIGHT CONVERSION

(71) Applicant: Halliburton Energy Services, Inc. ("HESI"), Duncan, OK (US)

(72) Inventors: Etienne M. Samson, Cypress, TX (US); John L. Maida, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 218 days.

(21) Appl. No.: 13/722,623

(22) Filed: Dec. 20, 2012

(65) Prior Publication Data

US 2014/0175272 A1    Jun. 26, 2014

(51) Int. Cl.
| | |
|---|---|
| *E21B 47/06* | (2012.01) |
| *E21B 41/00* | (2006.01) |
| *G02F 1/01* | (2006.01) |
| *G01V 8/24* | (2006.01) |
| *E21B 47/10* | (2012.01) |
| *E21B 47/12* | (2012.01) |

(52) U.S. Cl.
CPC .............. *G02F 1/0115* (2013.01); *E21B 41/00* (2013.01); *G01V 8/24* (2013.01); *E21B 47/06* (2013.01); *E21B 47/10* (2013.01); *E21B 47/123* (2013.01)

(58) Field of Classification Search
CPC ......... E21B 41/00; E21B 47/06; E21B 47/10; E21B 47/123; G01V 8/24; G02F 1/0115
USPC ........ 250/253, 256, 264, 269.1, 336.1, 458.1, 250/459.1; 356/432, 436, 440; 385/122, 385/123
See application file for complete search history.

(56) References Cited

U.S. PATENT DOCUMENTS

| | | | |
|---|---|---|---|
| 4,162,400 | A | 7/1979 | Pitts, Jr. |
| 5,037,172 | A | 8/1991 | Hekman et al. |
| 5,729,013 | A | 3/1998 | Bergren, III |
| 6,522,797 | B1 | 2/2003 | Siems et al. |

(Continued)

FOREIGN PATENT DOCUMENTS

| | | |
|---|---|---|
| WO | WO-00/12978 | 3/2000 |
| WO | WO-2007/066146 | 6/2007 |

(Continued)

OTHER PUBLICATIONS

Broeng, Jes, et al., "Photonic Crystal Fibers in the Market", The 16th Opto-Electrics and Communications Conference (Jul. 4, 2011), 2 pgs.

(Continued)

*Primary Examiner* — Mark R Gaworecki
(74) *Attorney, Agent, or Firm* — Krueger Iselin LLP

(57) ABSTRACT

A disclosed remote work system includes a light source and a nonlinear converter optically coupled to and remote from the light source. The nonlinear light converter converts a narrowband light pulse received from the light source to a converted spectrum light pulse. The system also includes a work element coupled to the nonlinear light converter. The work element performs a work operation using the converted spectrum light pulse. A related remote work method includes generating a narrowband light pulse and conveying the narrowband light pulse to a remote location. The method also includes converting the narrowband light pulse to a converted spectrum light pulse at the remote location. The method also includes performing a sense operation or work operation at the remote location using the converted spectrum light pulse.

19 Claims, 7 Drawing Sheets

(56) References Cited

U.S. PATENT DOCUMENTS

| | | |
|---|---|---|
| 6,591,025 B1 | 7/2003 | Siems et al. |
| 2004/0031923 A1* | 2/2004 | Sanders .................. 250/341.2 |
| 2004/0113104 A1 | 6/2004 | Maida et al. |
| 2004/0141420 A1 | 7/2004 | Hardage et al. |
| 2004/0163809 A1 | 8/2004 | Mayeu et al. |
| 2006/0081412 A1 | 4/2006 | Wright et al. |
| 2006/0215974 A1 | 9/2006 | Maida |
| 2007/0146866 A1 | 6/2007 | Wright |
| 2008/0073084 A1 | 3/2008 | Ringgenberg et al. |
| 2009/0002697 A1 | 1/2009 | Freese et al. |
| 2011/0088462 A1 | 4/2011 | Samson et al. |
| 2011/0116099 A1 | 5/2011 | Spross et al. |
| 2011/0290992 A1 | 12/2011 | Sato et al. |
| 2011/0298457 A1 | 12/2011 | Samson et al. |
| 2011/0308788 A1 | 12/2011 | Ravi et al. |
| 2012/0014211 A1 | 1/2012 | Maida et al. |
| 2012/0018167 A1 | 1/2012 | Konopczynski et al. |
| 2012/0061084 A1 | 3/2012 | Sweatman et al. |
| 2012/0147381 A1 | 6/2012 | Leblanc et al. |
| 2012/0205103 A1 | 8/2012 | Ravi et al. |
| 2012/0257475 A1 | 10/2012 | Luscombe et al. |
| 2014/0175272 A1 | 6/2014 | Samson et al. |

FOREIGN PATENT DOCUMENTS

| | | |
|---|---|---|
| WO | WO-2012/257475 | 10/2012 |
| WO | WO-2014/099054 | 6/2014 |

OTHER PUBLICATIONS

Garmire, Elsa, "Overview of Nonlinear Optics," Nonlinear Optics, Natalia Kamanina (Ed.), ISBN: 978-953-51-0131-4, InTech, DOI: 10.5772/37416. Available from: http://www.intechopen.com/books/nonlinear-optics/overview-of-nonlinear-optics, (2012), 1 pgs.

Maida, John L., et al., "Downhole Species Selective Optical Fiber Sensor Systems and Methods", U.S. Appl No. 13/253,788, filed Oct. 5, 2011, 23 pgs.

Maida, John L., et al., "Optical Casing Collar Locator Systems and Methods", U.S. Appl No. 13/226,578, filed Sep. 7, 2011, 30 pgs.

NKT Photonics, "Supercontinuum Generation in Photonics Crystal Fibers", (Jul. 2009), 10 pgs.

Samson, Etienne M., et al., Downhole Systems and Methods for Water Source Determination', U.S. Appl No. 13/418,455, filed Mar. 13, 2012, 27 pgs.

Sharp, David P., et al., "Casing Collar Locator with Wireless Telemetry Support", U.S. Appl No. 13/426,414, filed Mar. 21, 2012, 30 pgs.

Skinner, Neal G., et al., "Downhole Time Domain Reflectometry with Optical Components", U.S. Appl No. 13/655,607, filed Oct. 19, 2012, 32 pgs.

Teipel, J. et al., "Characteristics of supercontinuum generation in tapered fibers using femtosecond laser pulses", Institut für Angewandte Physik, Universität Bonn, Wegelerstr. 8, 53115 Bonn, Germany, (Jul. 16, 2003), 7 pgs.

"PCT search report and written opinion", dated Feb. 28, 2014, Appl No. PCT/US2013/058127, "Remote Work Methods and Systems Using Nonlinear Light Conversion," filed Sep. 5, 2013, 14 pgs.

Fedotov, Andrei B. et al., "Frequency-Tunable Supercontinuum Generation in Photonic-Crystal Fibers by Femtosecond Pulses of an Optical Parametric Amplifier", J. Opt. Soc. Am. B/vol. 19, No. 9/Sep. 2002, XP-002275995, (2002), pp. 2156-2164.

Hecht, Jeff "Fiber Lasers: The State of the Art", Laser Focus World, vol. 48, No. 4, Apr. 1, 2012, XP055102644, ISSN: 1043-8092 [retrieved from: http://www.laserfocusworld.com/articles/print/volume-48/issue-04/features/the-state-of-the-art.html], (2012), 24 pgs.

"US Non-Final Office Action", dated Mar. 16, 2015, U.S. Appl. No. 13/726,041, "Remote Sensing Methods and Systems Using Nonlinear Light Conversion and Sense Signal Transformation," filed Dec. 22, 2012, 12 pgs.

\* cited by examiner

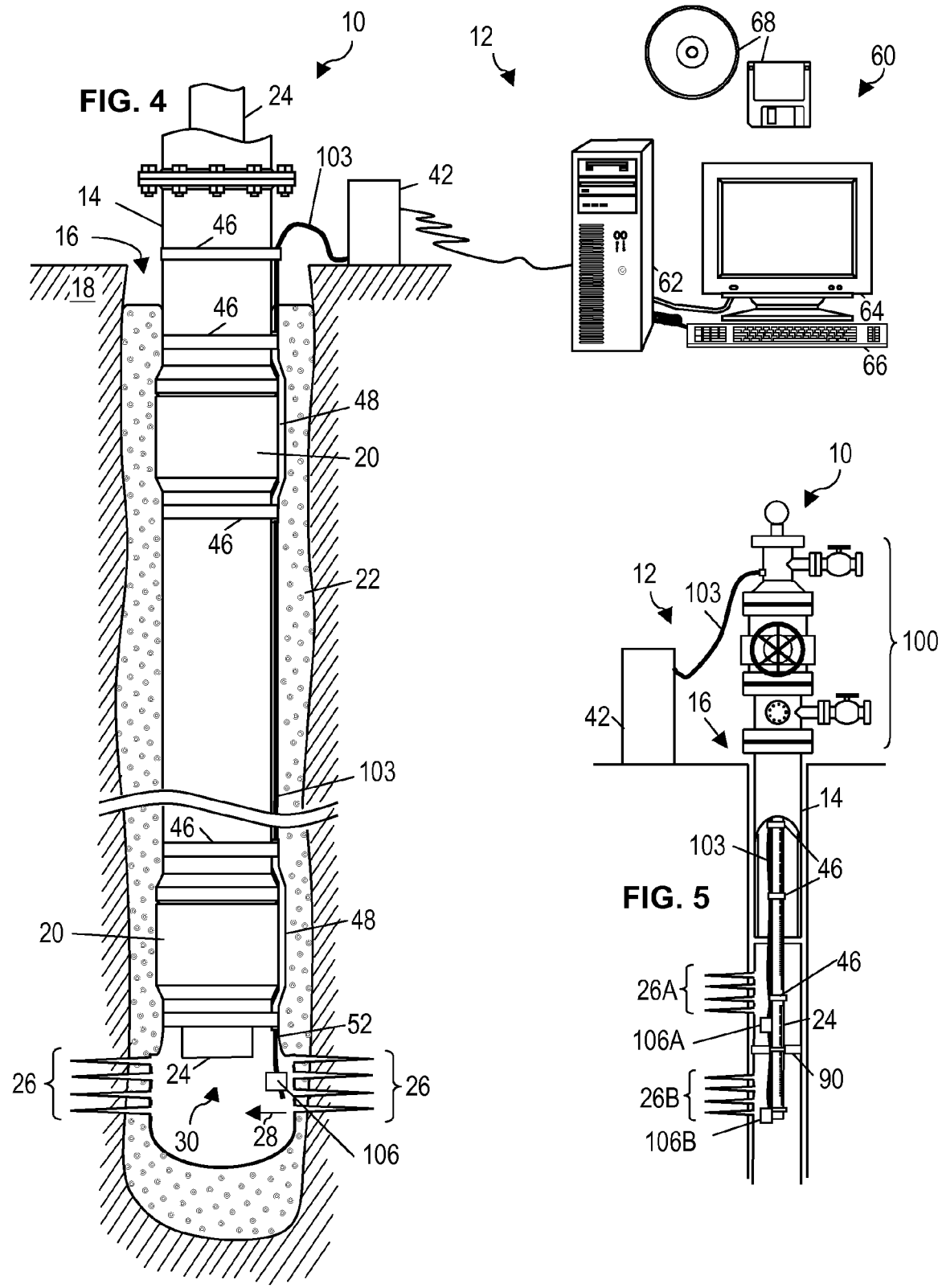

US 9,075,252 B2

REMOTE WORK METHODS AND SYSTEMS USING NONLINEAR LIGHT CONVERSION

BACKGROUND

Modern oil field operations demand a great quantity of information relating to the parameters and conditions encountered downhole. Such information typically includes characteristics of the earth formations traversed by a borehole, and data relating to the size and configuration of the borehole itself In general, sensor-based data logging may occur during various oil field operations including drilling, openhole logging, well completion, treatment applications, or production.

Various types of sense techniques are available to collect downhole data. Some optical sense techniques are desirable, but require a broadband light source. Simply conveying broadband light to a remote location is problematic due to the bandwidth limitations of optical fibers. Further, use of a broadband light source in a downhole environment involves electronics that are prone to failure in the extreme environment. Hence, certain optical sense techniques are regarded as infeasible.

BRIEF DESCRIPTION OF THE DRAWINGS

Accordingly, there are disclosed in the drawings and the following description specific examples of remote sensing methods and systems using nonlinear light conversion. In the drawings:

FIGS. 4-6 show illustrative well environments in which the remote sensing system of FIG. 1A and remote tool system of FIG. 1B may be employed.

Figure 1A:
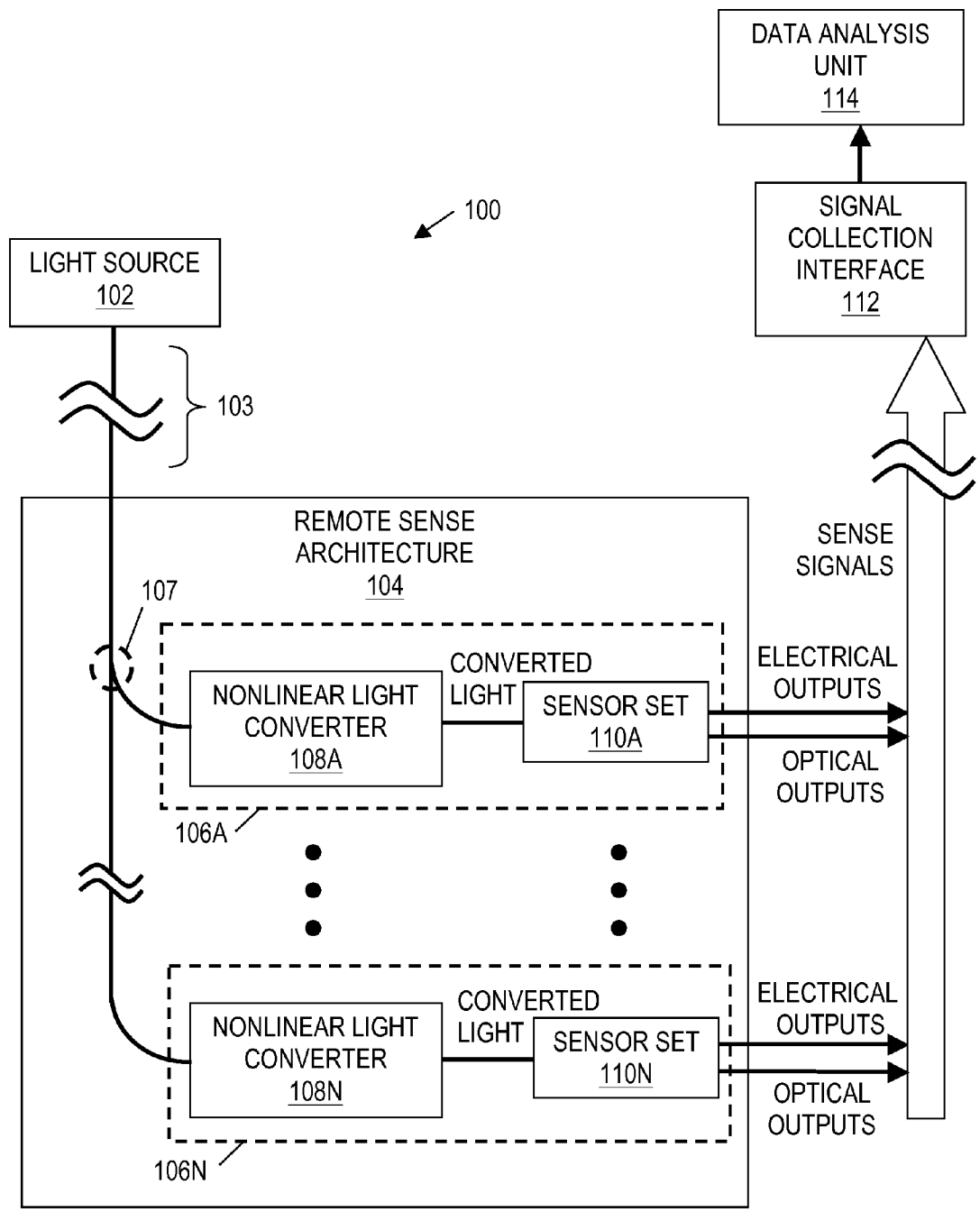
FIG. 1A is a block diagram of an illustrative remote sensing system.

It should be understood, however, that the specific embodiments given in the drawings and detailed description thereof do not limit the disclosure. On the contrary, they provide the foundation for one of ordinary skill to discern the alternative forms, equivalents, and modifications that are encompassed together with one or more of the given embodiments in the scope of the appended claims.

NOMENCLATURE

Certain terms are used throughout the following description and claims to refer to particular system components. This document does not intend to distinguish between components that differ in name but not function. The terms "including" and "comprising" are used in an open-ended fashion, and thus should be interpreted to mean "including, but not limited to . . . ".

The term "couple" or "couples" is intended to mean either an indirect or direct electrical, mechanical, or thermal connection. Thus, if a first device couples to a second device, that connection may be through a direct connection, or through an indirect connection via other devices and connections. Conversely, the term "connected" when unqualified should be interpreted to mean a direct connection. For an electrical connection, this term means that two elements are attached via an electrical path having essentially zero impedance.

The term "remote" is intended to mean a location that is inaccessible and/or far away. For example, a remote optical sensor as described herein may refer to an optical sensor that is in a dangerous or extreme location (e.g., a nuclear facility, a downhole environment, or a subsea environment), or that is far away from a point of reference. Thus, a remote optical sensor may be far away from a point of reference (such as an associated light source) without necessarily being inaccessible.

DETAILED DESCRIPTION

Disclosed herein are methods and systems using nonlinear light conversion to perform remote work operations such as sense operations or tool element operations (e.g., converted light may be used for sensor operations, heated tool element operations, or powered tool element operations. An example remote work system includes a nonlinear light converter optically coupled to a remote light source. The nonlinear light converter converts a narrowband light pulse received from the light source to an expanded spectrum and/or shifted spectrum light pulse. A remote work system includes a work element (e.g., a sensor or tool element) in situ with the nonlinear light converter to perform a work operation using the expanded spectrum and/or shifted spectrum light pulse. For example, the work element may be a sensor, a heated tool element, or a powered tool element as described herein. In some embodiments, remote work systems may include both sensors and tool elements. In such case, sensors, heated tool elements, and/or powered tool elements of the remote work system are configured to operate using the output of at least one nonlinear converter.

In at least some embodiments, a remote work system for downhole environments includes a surface light source and a downhole supercontinuum light converter such as a photonic crystal fiber (PCF) or a tapered fiber with a dispersive cladding. The output of the downhole supercontinuum light converter is used as input for a spectrometer, interferometer, imaging sensor, pressure sensor, and/or other optically driven parameter sensors in the downhole environment. Additionally or alternatively, the output of the downhole supercontinuum light converter is used to power a circuit or movable tool element. As another example, the output of the downhole supercontinuum light converter may be used to control heating for materials, sensors, or chambers in the downhole environment. In some embodiments, metaparticles may be employed to facilitate heating operations using the output of a downhole supercontinuum light converter.

Figure 1B:
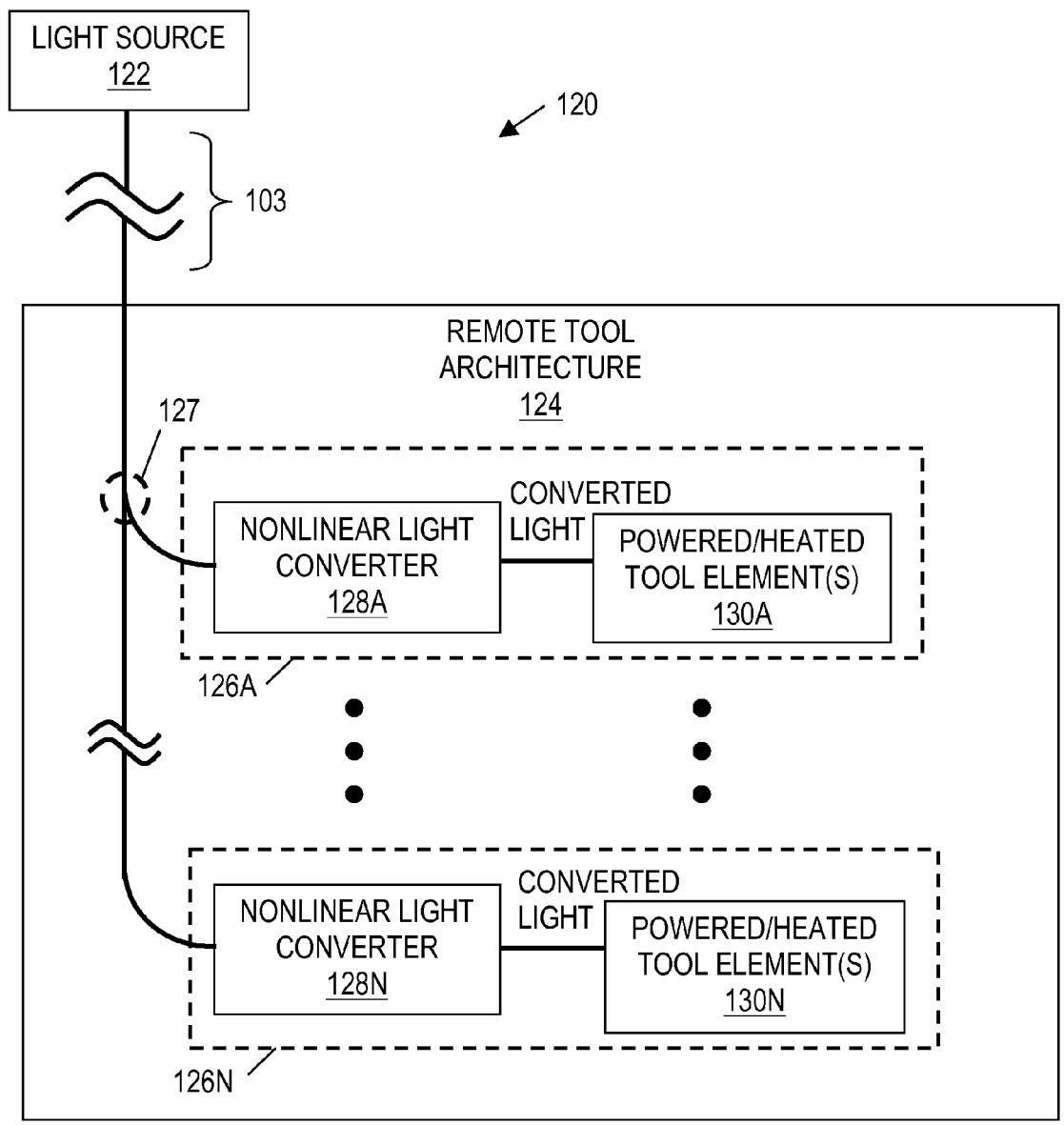
FIG. 1B is a block diagram of an illustrative remote tool system.

FIG. 1A is a block diagram of an illustrative remote sensing system 100, while FIG. 1B is a block diagram of an illustrative remote tool system 120. Systems 100 and 120 are examples of remote work systems as described herein, where the output of nonlinear converters is used to perform remote work operations. As shown, the remote sensing system 100 comprises a light source 102 that is optically coupled to an arrangement of one or more remotely located sensors (hereafter, "a remote sense architecture") via an optical waveguide cable 103 and splitters 107. For example, in some embodiments, the optical waveguide cable 103 includes one or more optical fibers. The illustrated remote sense architecture 104 includes different sensor zones 106A-106N, where each of the sensor zones 106A-106N includes a nonlinear light converter and a sensor set. More specifically, sensor zone 106A includes nonlinear light converter 108A and sensor set 110A, sensor zone 106B includes nonlinear light converter 108B and sensor set 110B, and so on. Although a plurality of sensor zones 106A-106N are shown in FIG. 1A, it should be understood that some remote sensing system embodiments may employ a single sensor zone.

The illustrated outputs from the sensor sets 110A-110N are labeled as electrical signals or optical signals. The output sense signals are transmitted in real-time to a signal collection interface 112 and data analysis unit 114, which are located remotely from the remote sense architecture 104. For example, the signal collection interface 112 and data analysis unit 114 may be at a surface location while the remote sense architecture 104 is downhole. This block diagram will be applied to specific examples in the description of FIGS. 4-6 below.

In different embodiments, the signal collection interface 112 and the data analysis unit 114 may be local or remote to each other. Similarly, the light source 102 may be local or remote to either the signal collection interface 112 or the data analysis unit 114. Further, in some embodiments, the output sense signals are stored in the downhole location rather than being transmitted in real-time to the surface. For example, the output sense signals may be stored as part of a downhole tool that is retrievable. Once the downhole tool has been retrieved, the stored data is accessible for analysis by data analysis unit 114.

As described herein, nonlinear light converters 108A-108N are employed in the illustrated remote sense architecture 104. Optical nonlinearities occur when the output of a material or device ceases to be a linear function of the input power, which is almost always the case for high enough intensities. The nonlinearity may cause a light-induced change in refractive index or absorption of the medium or it may cause new frequencies to be generated. Attributes that affect nonlinearity include the character of the medium, atom-light interaction, optics geometries, and device geometries. For more information regarding nonlinear optics reference may be had to Elsa Garmire (2012), Overview of Nonlinear Optics, Nonlinear Optics, Dr. Natalia Kamanina (Ed.), ISBN:978-953-51-0131-4, InTech, Available from: http://www.intechopen.com/books/nonlinear-optics/overview-of-nonlinear-optics.

Use of nonlinear light conversion as described herein involves converting a narrowband light pulse received from a remote light source to a broadened spectrum and/or shifted spectrum light pulse. While narrowband light pulses can be successfully conveyed to a remote location via a fiber optic cable, they are not suitable for most optical sense operations. In contrast, broadened spectrum light pulses output from the disclosed nonlinear light converters cannot be conveyed long distances without severe attenuation, but can be conveyed short distances to enable optical sensors of the remote sense architecture 104 to operate correctly. Similarly, shifted spectrum light pulses output from the disclosed nonlinear light converters may not propagate as far as narrowband light pulses, but are better suited to operate certain optical sensors.

As shown in FIG. 1B, the remote tool system 120 comprises a light source 122 that is optically coupled to an arrangement of one or more remotely located tool elements (hereafter, "a remote tool architecture") via an optical waveguide cable 103 and splitters 127. The illustrated remote tool architecture 124 includes different tool zones 126A-126N, where each of the tool zones 126A-126N includes a nonlinear light converter and powered or heated tool elements. More specifically, tool zone 126A includes nonlinear light converter 128A and powered/heated tool element(s) 130A, tool zone 126B includes nonlinear light converter 128B and powered/heated tool element(s) 130B, and so on.

Although a plurality of tool zones 126A-126N are shown in FIG. 1B, it should be understood that some remote sensing system embodiments may employ a single tool zone. As previously mentioned, a combination of systems 100 and 120 is possible. In such case, sensors, heated tool elements, and/or powered tool elements of a remote sensing and tool system are configured to operate using the output of at least one nonlinear converter. In some embodiments, powered tool elements or heated tool elements of system 120 generate signals related to their operations. These signals may be transmitted to a signal collection interface and data analysis unit (similar to signal collection interface 112 and data analysis unit 114 of system 100).

Figure 2A:
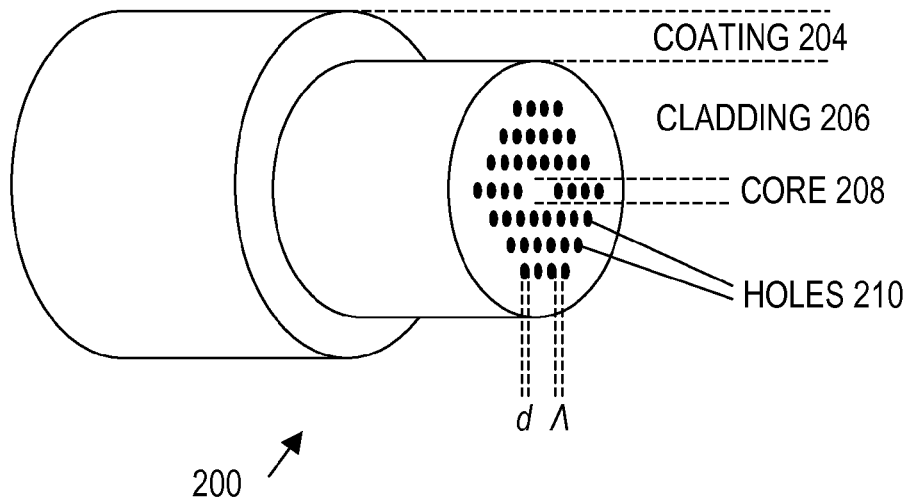
FIGS. 2A-2C show illustrative nonlinear light converters for the systems of FIGS. 1A and 1B.
Figure 2B:
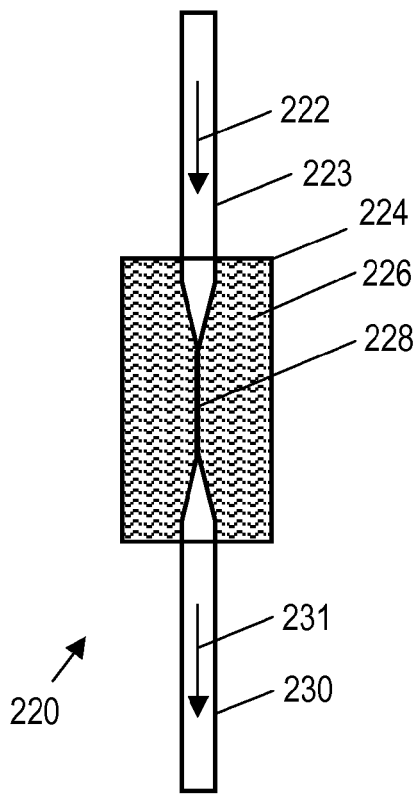
Figure 2C:
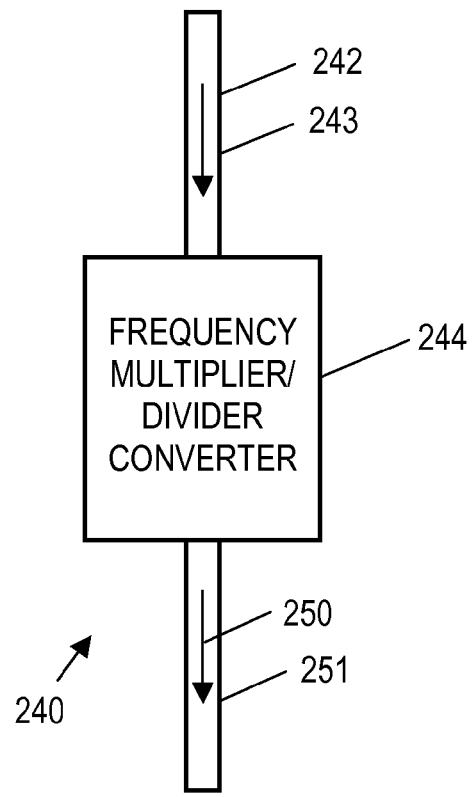
Figure 3A:
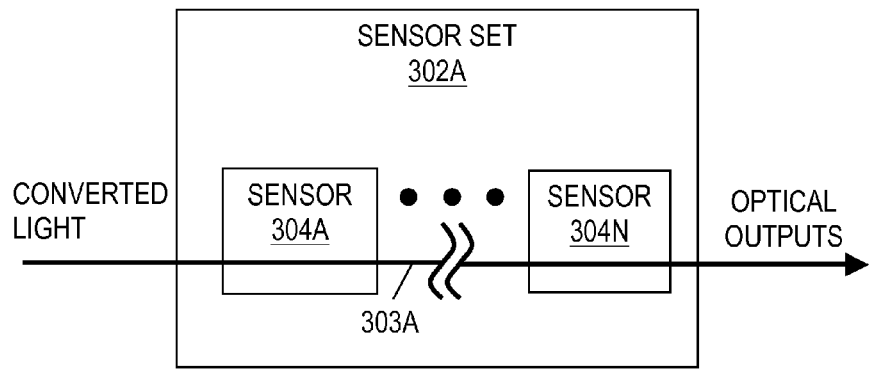
FIGS. 3A-3E show block diagrams of illustrative sensor sets for the remote sensing system of FIG. 1A.
Figure 3B:
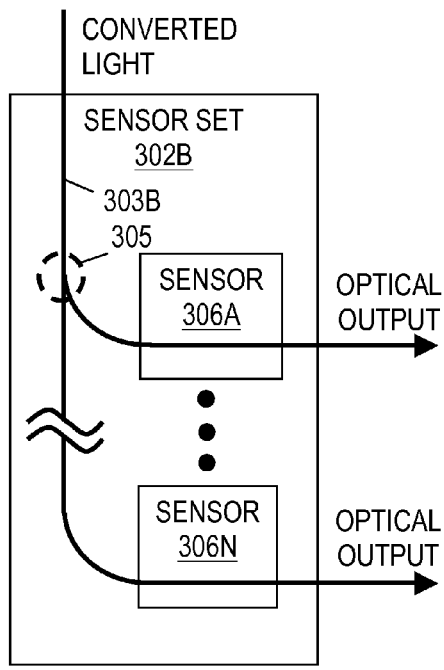
Figure 3C:
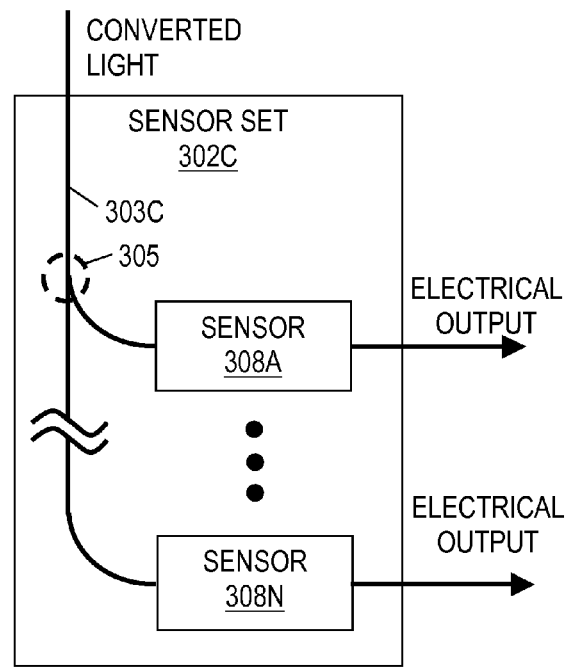
Figure 3D:
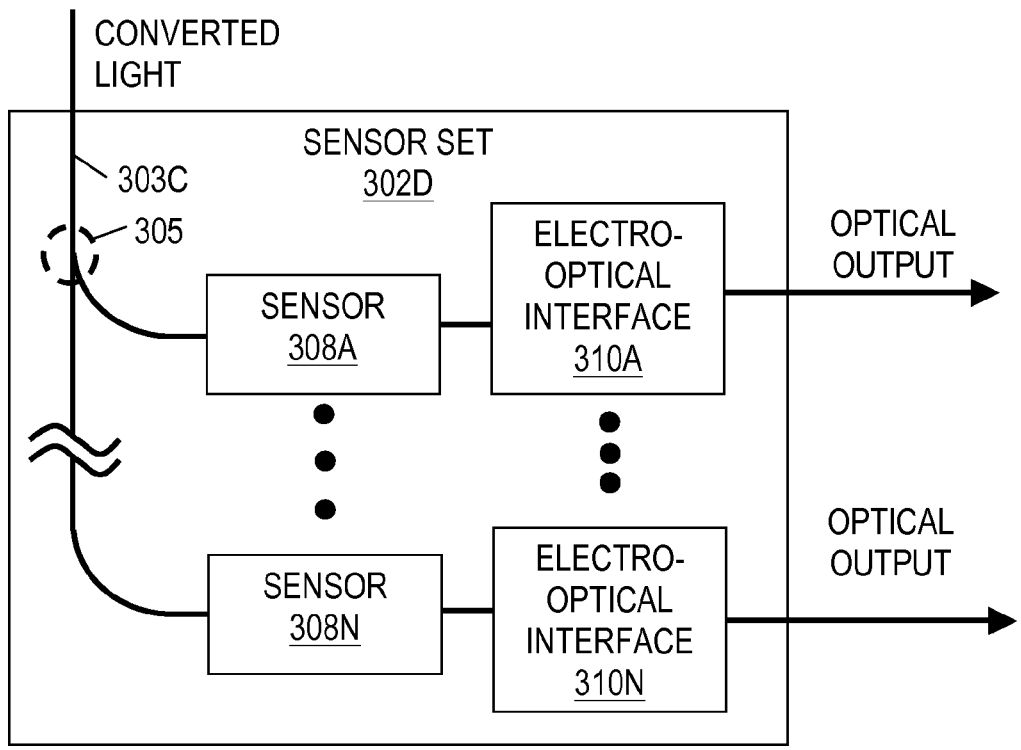
Figure 3E:
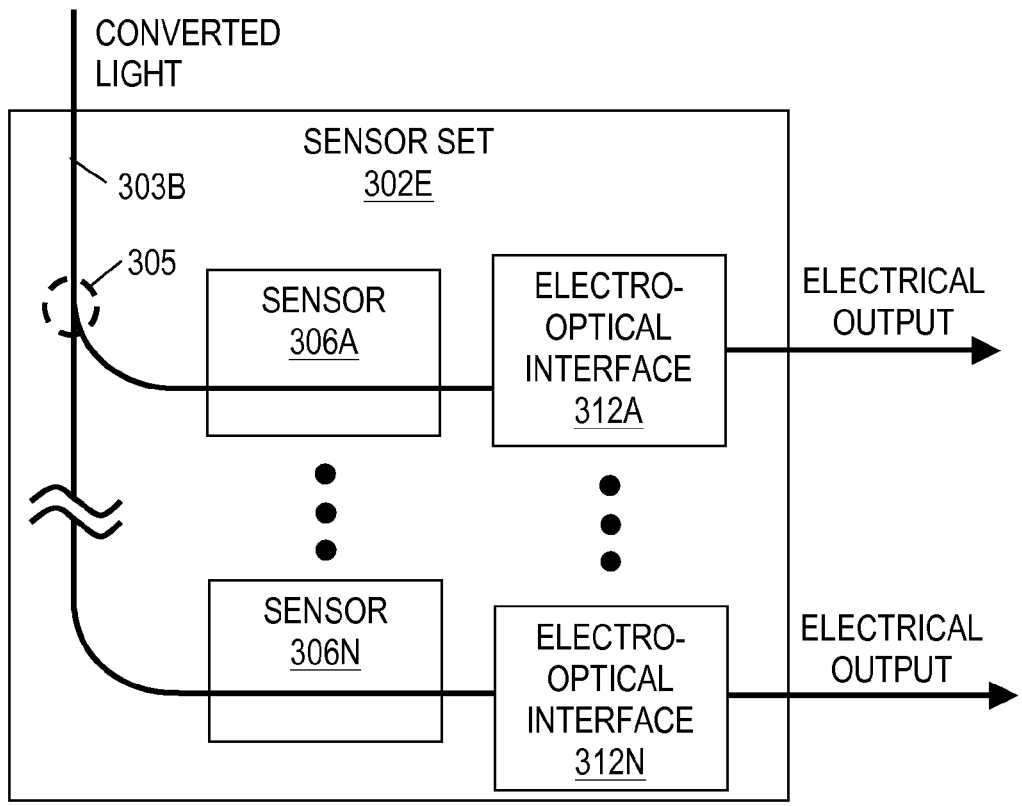

FIGS. 2A-2C show illustrative nonlinear light converters 200, 220, and 240 for the remote sensing system 100 or remote tool system 120 of FIGS. 1A and 1B. The nonlinear light converter 200 of FIG. 2A corresponds to a photonic crystal fiber (PCF) that operates as a supercontinuum light source. As shown, the nonlinear light converter 200 comprises coating 204, cladding 206, and core 208. The cladding 206 has various holes 210 with hole-size d and hole-pitch $\Lambda$, which may vary for different PCF designs. In operation, narrowband light traveling through a length of the nonlinear light converter 200 is modified due to the dispersive effect of the cladding 206 with holes 210. In accordance with some embodiments, a length (e.g., 10-20 meters) of the nonlinear light converter 200 is used to convert a narrowband light pulse to a supercontinuum (broadband) light pulse that is used for remote work operations as described herein. Various factors affect generation of supercontinua by the nonlinear light converter 200 including the dispersion effect of the cladding 206 relative to the pumping wavelength, the pulse length, and the peak power. For more information regarding supercontinuum generation with PCFs reference may be had to Kim P. Hansen and Rene E. Kristiansen, Supercontinuum Generation in Photonic Crystal Fibers, available at http://www.thorlabs.com/images/TabImages/10736-A02.pdf.

The nonlinear light converter 220 of FIG. 2B corresponds to a tapered fiber with dispersive cladding that operates as a supercontinuum light source. In FIG. 2B, narrowband light 222 traveling through waveguide 223 reaches a dispersion cladding container 224 in which a tapered waveguide 228 resides. The dispersion cladding container 224 is filled with a dispersive material 226 such as heavy water. The narrowband light 222 entering the dispersion cladding container 224 is modified by the dispersive material 226 such that a supercontinuum light pulse 231 is output to waveguide 230. Thus, nonlinear light converter 220 is used to convert a narrowband light pulse to a supercontinuum light pulse that is used for remote work operations. For more information regarding supercontinuum generation with tapered fibers reference may be had to J. Teipel et al., Characteristics of supercontinuum generation in tapered fibers using femtosecond laser pulses, Appl. Phys. B 77 245-251 (2003).

The nonlinear light converter 240 of FIG. 2C corresponds to a frequency multiplier converter or frequency divider converter that operates as a shifted spectrum light source. In FIG. 2C, narrowband light 243 traveling through waveguide 242 reaches the frequency converter 244. The frequency converter 244 includes a nonlinear material that generates higher or lower frequency light in response to receiving the narrowband light 243. For example, the frequency converter 244 may include a frequency doubler material such as lithium niobate, lithium tantalate, potassium titanyl phosphate, or lithium tribolate. In alternative embodiments, the frequency converter 244 may include a frequency tripler material such as potassium dihydrogen phosphate. In accordance with some embodiments, nonlinear light converter 240 is used to convert a narrowband light pulse to a shifted spectrum light pulse that is used for remote work operations.

The remote sensing system 100 may implement one or more of any of the nonlinear light converters 200, 220, and 240 for each of the sensor zones 106A-106N. For example, if nonlinear light converter 200 corresponds to nonlinear light converter 108A of sensor zone 106A, then the sensor set 110A may perform sense operations using a supercontinuum light pulse output from the nonlinear light converter 200. Likewise, if nonlinear light converter 220 corresponds to nonlinear light converter 108A of sensor zone 106A, then the sensor set 110A may perform sense operations using a supercontinuum light pulse output from the nonlinear light converter 220. In an alternative example, if nonlinear light converter 240 corresponds to nonlinear light converter 108A of sensor zone 106A, then the sensor set 110A may perform sense operations using a shifted spectrum light pulse output from the nonlinear light converter 240.

Likewise, the remote tool system 120 may implement one or more of any of the nonlinear light converters 200, 220, and 240 for each of the tool zones 126A-126N. For example, if nonlinear light converter 200 corresponds to nonlinear light converter 128A of tool zone 126A, then the powered or heated tool element(s) 130A may perform tool operations using a supercontinuum light pulse output from the nonlinear light converter 200. Likewise, if nonlinear light converter 220 corresponds to nonlinear light converter 128A of sensor zone 126A, then the powered or heated tool element(s) 130 may perform tool operations using a supercontinuum light pulse output from the nonlinear light converter 220. In an alternative example, if nonlinear light converter 240 corresponds to nonlinear light converter 128A of tool zone 126A, then the powered or heated tool element(s) 130A may perform tool operations using a shifted spectrum light pulse output from the nonlinear light converter 240.

FIGS. 3A-3E show block diagrams of illustrative sensor sets 302A-302E suitable for the remote sensing system 100 of FIG. 1A. In sensor set 302A, a plurality of sensors 304A-304N are arranged in series along an optical waveguide 303A that conveys converted light from a nonlinear light converter (e.g., one of the converters 108A-108N). The sensor set 302A provides optical outputs from the sensors 304A-304N, which perform sensing operations that modify received light from nonlinear converter in response to the presence of particular chemicals, wavelengths, pressures, strains, or other physical parameters. As an example, one or more of the sensors 304A-304N may correspond to an ion selective fiber (ISF) sensor that modifies received light depending on a concentration of a predetermined chemical species or ion. As another example, one or more of the sensors 304A-304N may correspond to a wavelength filter (e.g., a reflector or grating) that modifies received light according to a predetermined design. The operation of the wavelength filter is affected by physical parameters such as temperature, pressure, shock, or strain, and thus changes in the operation of the filter can be used to monitor changes in the physical environment in which the wavelength filter resides. Integrated Computation Elements (ICEs) are one type of wavelength filter that may correspond to sensors 304A-304N. ICEs can be constructed, for example, with a series of layers having thicknesses and indices of refraction designed to interfere constructively or destructively at desired wavelengths to provide an encoded pattern specifically for the purpose of interacting with light and providing an optical spectrum matching operation. When a match occurs, the intensity of light output from the ICE is higher.

In sensor set 302B, a plurality of sensors 306A-306N are arranged in parallel optical branches that split off from an optical waveguide 303B and that convey converted light from a nonlinear light converter (e.g., one of the converters 108A-108N). Optical splitters 305 may be employed, for example, to direct light to different optical branches. The sensor set 302B provides optical outputs from the sensors 306A-306N, which perform sensing operations that modify received light in response to particular chemicals, wavelengths, pressures, strains, or other physical parameters. As an example, the sensors 306A-306N may correspond to the ISF sensors or wavelength filters as mentioned previously.

Sensor set 302C is similar to sensor set 302B, except that sensors 308A-308N output electrical signals instead of optical signals. Thus, converted light is provided to the sensor set 302C, and electrical signals are output from the sensors 308A-308N in response to particular chemicals, wavelengths, pressures, strains, or other physical parameters.

In sensor set 302D, the same optical waveguide 303C and sensors 308A-308N as described for sensor set 302C are illustrated. The sensor set 302D differs from sensor set 302C due to the addition of electro-optical interfaces 310A-310N, which convert electrical signals output from sensors 308A-308N to corresponding optical signals.

In sensor set 302E, the same optical waveguide 303B and sensors 306A-306N as described for sensor set 302B are illustrated. The sensor set 302E differs from sensor set 302B due to the addition of electro-optical interfaces 312A-312N, which convert optical signals from sensors 306A-306N to corresponding electrical signals. Thus, sensor sets 302D and 302E illustrate that optical signals output from sensors may be converted to electrical signals or vice versa. Such conversion may be performed to facilitate storing sense signals or to facilitate transmitting sense signals from the remote architecture 104 to another location for processing and/or display.

The sensor sets 302A-302E may correspond to any of the sensor sets 110A-110N in FIG. 1. Some remote sensing systems 100 may employ one type of the sensor sets 302A-302E, while other remote sensing systems 100 employ another type of the sensor sets 302A-302E. Further, some remote sensing systems 100 may employ different combinations of the sensors sets 302A-302E.

Figure 6:
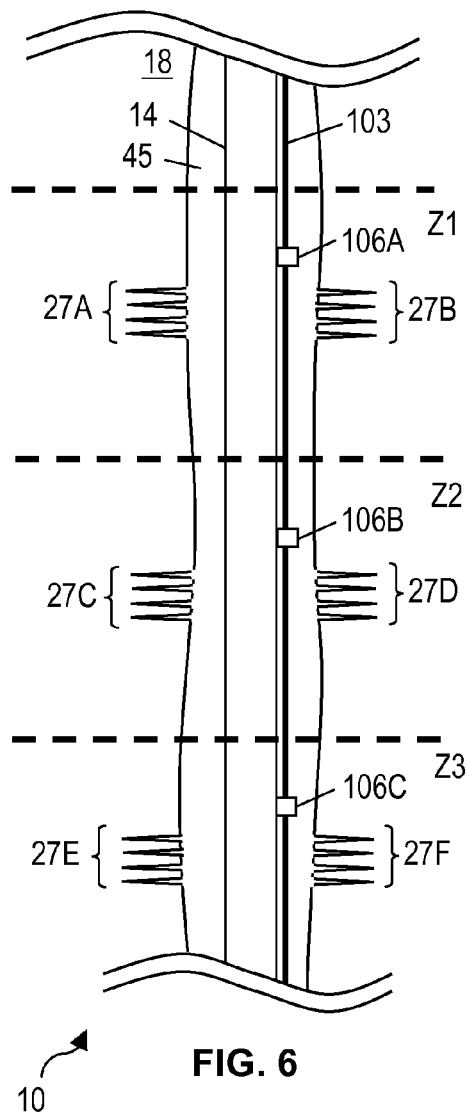

FIGS. 4-6 show illustrative well environments in which the remote sensing system 100 of FIG. 1A or the remote tool system of FIG. 1B may be employed. FIG. 4 shows a production well 10 equipped with an illustrative downhole work system 12 that includes remote sensing system 100 and/or remote tool system 120. The well 10 shown in FIG. 4 has been constructed and completed in a typical manner, and it includes a casing string 14 positioned in a borehole 16 that has been formed in the earth 18 by a drill bit. The casing string 14 includes multiple tubular casing sections (usually about 30 foot long) connected end-to-end by couplings 20. Within the well 10, cement 22 has been injected between an outer surface of the casing string 14 and an inner surface of the borehole 16 and allowed to set. A production tubing string 24 has been positioned in an inner bore of the casing string 14.

The well 10 is adapted to guide a desired fluid (e.g., oil or gas) from a bottom of the borehole 16 to the surface of the earth 18. Perforations 26 have been formed at a bottom of the borehole 16 to facilitate the flow of a fluid 28 from a surrounding formation (i.e., a "formation fluid") into the borehole and thence to the surface via an opening 30 at the bottom of the production tubing string 24. Though only one perforated zone is shown, many production wells may have multiple such zones, e.g., to produce fluids from different formations.

In some embodiments, the downhole work system 12 is adapted to perform monitoring operations such as detecting physical parameters such as chemicals, wavelengths, pressures, strains, or other physical parameters. In such case, the downhole work system 12 may enable monitoring of physical parameters over time or at particular moments in time. In addition, or in alternative embodiments, the downhole work system 12 is adapted to perform powered and/or heated tool element operations as described herein. In some embodiments, metaparticles that react to light by releasing heat may be employed to facilitate heating operations performed by the downhole work system 12.

In the embodiment of FIG. 4, the downhole work system 12 includes a sensor/tool zone 106 (corresponding to one or more of zones 106A-106N or 126A-126N) near the fluid 28 at the bottom of the borehole 16. The sensor/tool zone 106 is coupled to an interface 42 via optical waveguide cable 103. In some embodiments, the interface 42 is located on the surface of the earth 18 near the wellhead, i.e., a "surface interface" and includes light source 102.

In the embodiment of FIG. 4, the optical waveguide cable 103 extends along an outer surface of the casing string 14 and is held against the outer surface of the casing string 14 at spaced apart locations by multiple bands 46 that extend around the casing string 14. A protective covering 48 may be installed over the optical waveguide cable 103 at each of the couplings of the casing string 14 to prevent the cable from being pinched or sheared by the coupling's contact with the borehole wall. Such protective coverings 48 are held in place by two of the bands 46 installed on either side of coupling 20.

In at least some embodiments, the optic waveguide cable 103 terminates at surface interface 42 with an optical port adapted for coupling the optical waveguide cable 103 to a light source (e.g., light source 102). The light source 102 of surface interface 42 transmits light along the optical waveguide cable 103 to the sensor/tool zone 106, which operates to convert a narrowband light pulse transmitted from the surface interface 42 to a broadened spectrum and/or shifted spectrum light pulse. Work elements (sensors or tools) included with the sensor/tool zone 106 perform sense operations, powered tool element operations, and/or heated tool element operations using the broadened spectrum and/or shifted spectrum light pulse.

In some embodiments, the optical waveguide cable 103 terminates at surface interface 42 with an optical port adapted for coupling the optical waveguide cable 103 to a light source (e.g., light source 102). Further, the optical waveguide cable 103 may include sufficient fibers or transmission lines to enable sense signals to be transmitted back to the surface interface 42, which may include the sense signal collection interface 114. As an example, the surface interface 42 may include an optical port, a detector, a buffer, and/or other signal collection means coupled to the optical waveguide cable 103 to produce electrical output signals corresponding to received sense signals.

The illustrative downhole work system 12 of FIG. 4 further includes a computer 60 coupled to the surface interface 42 to control monitoring/tool operations. The illustrated computer 60 includes a chassis 62, an output device 64 (e.g., a monitor as shown in FIG. 4, or a printer), an input device 66 (e.g., a keyboard), and information storage media 68 (e.g., magnetic or optical data storage disks). However, the computer may be implemented in different forms including, e.g., an embedded computer permanently installed as part of the surface interface 42, a portable computer that is plugged into the surface interface 42 as desired to collect data, a remote desktop computer coupled to the surface interface 42 via a wireless link and/or a wired computer network, a mobile phone/PDA, or indeed any electronic device having a programmable processor and an interface for I/O.

The computer 60 receives electrical output signals produced by the surface interface 42 that correspond to signals from the sensor/tool zone 106, and determines downhole conditions related to the physical parameters or work element operations indicated by the received signals. The computer 60 also may display results for one or more downhole zones. Further, the computer 60 or an operator may update operations for drilling, well completion, formation treatment, or production based on the determined downhole conditions or work element operations.

In some embodiments, the information storage media 68 stores a software program for execution by computer 60. The instructions of the software program may cause the computer 60 to organize or display information regarding downhole conditions based on the sense signals collected from surface interface 42. Further, the software program may cause the computer 60 to display results including downhole conditions or work element operations over time for one or more zones. Further, the software program may cause the computer 60 or an operator to update operations for drilling, well completion, formation treatment, or production based on the determined downhole conditions.

FIG. 5 shows an alternative embodiment of a downhole work system 12, where the optical waveguide cable 103 is strapped to the outside of the production tubing 24 rather than the outside of casing 14. Two perforations 26A and 26B have been created in the borehole 16 to facilitate obtaining formation fluids from two different zones. Formation fluid from a first of the two zones enters the production tubing 24 via the perforation 26A, and formation fluid from the other zone enters the production tubing 24 via the perforation 26B. A packer 90 seals an annulus around the production tubing 24 and defines two different production zones. A first sensor zone 106A is positioned on one side of the packer 90 adjacent the perforation 26A, and a second sensor zone 106B is positioned on an opposite side of the packer 90 adjacent the perforation 26B. The sensor zones 106A and 106B operate as disclosed herein. Briefly, narrowband light received by the sensor zones 106A and 106B is converted to spectrum shifted lights pulses, and the broadened spectrum and/or shifted spectrum light pulses are used for work element operations within sensor zones 106A and 106B.

In the embodiment of FIG. 5, the sensor zones 106A and 106B are both coupled to the surface interface 42 via the optical waveguide cable 103. The optical waveguide cable 103 exits through an appropriate port in a "Christmas tree" 100, i.e., an assembly of valves, spools, and fittings connected to a top of a well to direct and control a flow of fluids to and from the well. The optical waveguide cable 103 extends along the outer surface of the production tubing 24, and is held against the outer surface of the production tubing 24 at spaced apart locations by multiple bands 46 that extend around the production tubing 24. In other embodiments, the sensor zones 106A and 106B may be coupled to the surface interface 42 via different optic waveguide cables.

FIG. 6 shows a distribution of sensor/tool zones 106A-106C along a section of a well 10. The zones (Z1-Z3) may be created by any known zoning mechanism. In some embodiments, Z1-Z3 are connected along an annular 45 between casing string 14 and formation 18. As shown, one or more fiber optic cables 103 may extend to the zones to enable sense operations or work element operations as described herein. Sense operations or work element operations may be performed near perforations 27A and 27B of Z1, near perforations 27C and 27D of Z2, and/or near perforations 27D and 27E of Z3. More specifically, sensor/tool zone 106A may perform sense operations and/or other work element operations for Z1, sensor/tool zone 106B may perform sense operations and/or other work element operations for Z2, and sensor/tool zone 106C may perform sense operations and/or other work element operations for Z3. As desired, additional sensor/tool zones 106 may be employed in one or more of zones Z1-Z3 (e.g., to enable higher resolution work element operations or downhole condition estimates to be made). Further, each sensor/tool zone may employ a variety of sensors or other work elements. In different embodiments, zones Z1-Z3 may vary with respect to size, the number of perforations, the number of sensor/tool zones 106, and/or the number of work elements in different sensor/tool zones 106.

Figure 7:
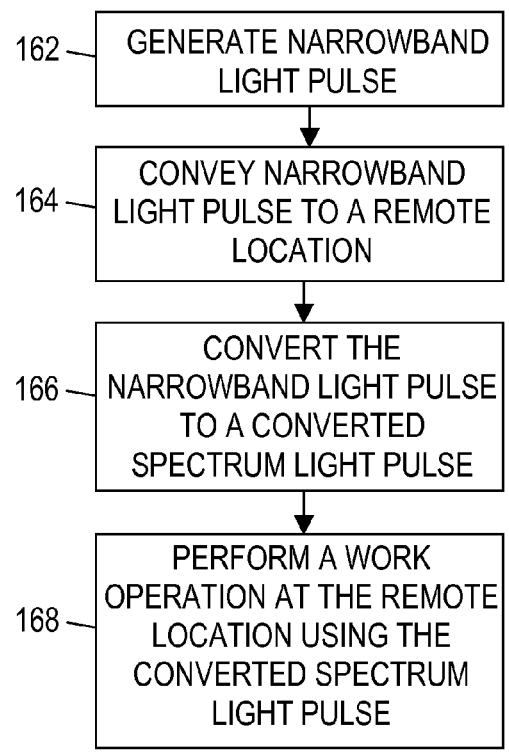
FIG. 7 shows an illustrative remote work method.

FIG. 7 shows an illustrative remote work method 160. As shown, the method 160 comprises generating a narrowband light pulse at block 162. The narrowband light pulse may be generated, for example, by a laser. At block 164, the narrow band light pulse is conveyed to a remote location such as a downhole environment or other extreme environment. At block 166, the narrowband light pulse is converted to a broadened spectrum and/or shifted spectrum light pulse. The conversion may be performed by a nonlinear light converter as described herein. At block 168, a work operation is performed at the remote location using the spectrum shifted light pulse. The work operation may be performed by various sensors as described herein and results in optical signals or electrical signals that can be correlated with particular chemicals, wavelengths, pressures, strains, or other physical parameters. Additionally or alternatively, the work operation may be performed by powering and/or heating a tool element using a converted spectrum light pulse output from a nonlinear converter as described herein.

Numerous modifications, equivalents, and alternatives will become apparent to those skilled in the art once the above disclosure is fully appreciated. For example, though the methods disclosed herein have been shown and described in a sequential fashion, at least some of the various illustrated operations may occur concurrently or in a different sequence, with possible repetition. It is intended that the following claims be interpreted (where applicable) to embrace all such modifications, equivalents, and alternatives.

What is claimed is:

1. A remote work system, comprising:
   a light source;
   a nonlinear light converter optically coupled to and remote from the light source, wherein the nonlinear light converter converts a narrowband light pulse received from the light source to a converted spectrum light pulse corresponding to a supercontinuum light pulse or a shifted spectrum light pulse; and
   a work element in situ with and coupled to the nonlinear light converter, wherein the work element performs an operation using the converted spectrum light pulse.

2. The remote work system of claim 1, wherein the nonlinear light converter comprises a photonic crystal fiber that converts the narrowband light pulse to a supercontinuum light pulse.

3. The remote work system of claim 1, wherein the nonlinear light converter comprises a tapered optical fiber with a dispersive cladding that converts the narrowband light pulse to a supercontinuum light pulse.

4. The remote work system of claim 1, wherein the nonlinear light converter comprises a frequency multiplier component or frequency divider component, and wherein the converted spectrum light pulse is shifted relative to the narrowband light pulse based on the frequency multiplier component or frequency divider component.

5. The remote work system of claim 1, wherein the work element comprises an integrated computation element (ICE) configured to perform a fluid analysis operation using the converted spectrum light pulse.

6. The remote work system of claim 1, wherein the work element comprises a sensor configured to perform a spectroscopy operation or chemical analysis operation using the converted spectrum light pulse.

7. The remote work system of claim 1, wherein the work element comprises a sensor configured to perform a sense operation using the converted spectrum light pulse, wherein the sense operation is selected from the list consisting of performing a filter interrogation operation, performing an interferometer operation, performing an imaging operation, and performing a pressure sense operation.

8. The remote work system of claim 1, wherein the work element comprises a tool element configured to perform a heated tool element operation using the converted spectrum light pulse.

9. The remote work system of claim 1, wherein the work element comprises a tool element configured to performed a powered tool element operation using the converted spectrum light pulse.

10. The remote work system of claim 1, further comprising:
    a plurality of a nonlinear light converters optically coupled to and remote from the light source; and
    a plurality of work elements in situ with and coupled to the nonlinear light converter, wherein at least some of the work elements are configured to perform sense operations, at least some of the work elements are configured to perform heated tool element operations, and at least some of the work elements are configured to performed powered tool element operations.

11. The remote work system of claim 1, wherein the nonlinear light converter and the work element are part of a downhole sensing architecture comprising a plurality of downhole nonlinear light converters optically coupled to and remote from the light source, and wherein each of the plurality of downhole nonlinear light converters is configured to provide a broadened spectrum light pulse to a distinct work element.

12. A remote work method, comprising:
    generating a narrowband light pulse;
    conveying the narrowband light pulse to a remote location;
    converting the narrowband light pulse to a converted spectrum light pulse at the remote location; and
    performing a work operation at the remote location using the converted spectrum light pulse, wherein the converted spectrum light pulse corresponds to a supercontinuum light pulse or a shifted spectrum light pulse.

13. The remote work method of claim 12, wherein performing the work operation using the converted spectrum light pulse comprises performing at least one of performing a spectroscopy operation or chemical analysis operation, and performing a filter interrogation operation or interferometer operation.

14. The remote work method of claim 12, wherein performing the work operation using the converted spectrum light pulse comprises performing at least one of performing an imaging operation and performing a pressure sense operation.

15. The remote work method of claim 12, wherein performing a work operation using the converted spectrum light pulse comprises performing a heated tool element operation with metaparticles.

16. The remote work method of claim 12, wherein performing a work operation using the converted spectrum light pulse comprises performing a powered tool element operation.

17. The remote work method of claim 12, further comprising:
    conveying the narrowband light pulse to a plurality of downhole supercontinuum light converters;
    converting the narrowband light pulse to a plurality of supercontinuum light pulses using the downhole supercontinuum light converters; and
    performing a plurality of downhole sense operations using the supercontinuum light pulses.

18. A downhole monitoring system, comprising:
    a surface light source; and
    a plurality of downhole sensor zones, each of the downhole sensor zones having a nonlinear light converter optically coupled to the surface light source and at least one sensor,
    wherein each of the nonlinear light converters is configured to convert narrowband light pulses received from the surface light source to broadened spectrum light pulses, and
    wherein each of the sensors is configured to perform sense operations using broadened spectrum light pulses.

19. A downhole tool system, comprising:
    a surface light source; and
    a plurality of downhole tool zones, each of the downhole tool zones having a nonlinear light converter optically coupled to the surface light source and at least one tool element,
    wherein each of the nonlinear light converters is configured to convert narrowband light pulses received from the surface light source to broadened spectrum light pulses, and
    wherein each of the tool elements is configured to perform a powered tool element operation or heated tool element operation using broadened spectrum light pulses.

* * * * *